United States Patent [19]

White

[11] 4,118,403

[45] Oct. 3, 1978

[54] RECOVERY OF MALEIC ANHYDRIDE

[75] Inventor: James E. White, Coshocton, Ohio

[73] Assignee: Monsanto Company, St. Louis, Mo.

[21] Appl. No.: 742,936

[22] Filed: Nov. 18, 1976

[51] Int. Cl.$^2$ ............................................ C07D 307/60
[52] U.S. Cl. ................................................ 260/346.76
[58] Field of Search .................................. 260/346.8 M

[56] References Cited

U.S. PATENT DOCUMENTS 2,942,005   6/1960   Brown et al. .................... 260/346.8

*Primary Examiner*—Henry R. Jiles
*Assistant Examiner*—Bernard Dentz
*Attorney, Agent, or Firm*—J. C. Logomasini; P. L. Passley; S. M. Tarter

[57] ABSTRACT

Maleic anhydride is recovered in high yields from gaseous mixtures containing the maleic anhydride in the vapor phase by cooling the gaseous mixture containing the maleic anhydride to a temperature above the dew point of water in the gaseous mixture, and then scrubbing the gaseous mixture with a solvent which comprises a phthalate ester, preferably dibutyl phthalate, and up to 10 weight percent phthalic anhydride. Thereafter, the maleic anhydride is stripped from the solvent in a one-step operation, and the solvent is thereafter recycled to the scrubbing step.

8 Claims, 1 Drawing Figure

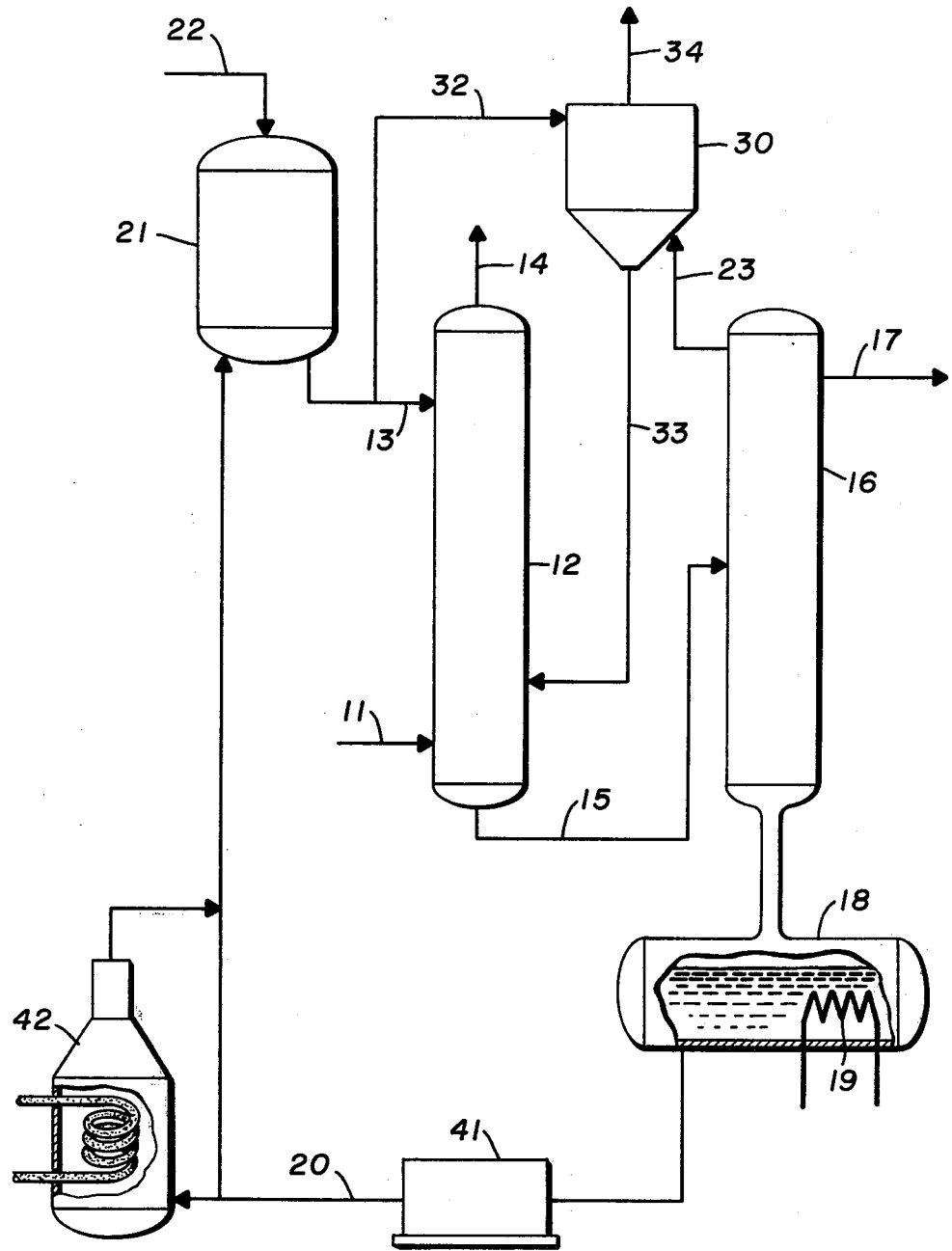

RECOVERY OF MALEIC ANHYDRIDE

BACKGROUND OF THE INVENTION

This invention relates to the recovery of maleic anhydride, and particularly to the recovery of maleic anhydride from gaseous mixtures containing maleic anhydride in the vapor phase using an organic solvent.

Maleic anhydride is of significant commercial interest throughout the world. It is used alone or in combination with other acids in the manufacture of alkyd and polyester resins. It is also a versatile intermediate for chemical synthesis. Significant quantities of maleic anhydride are produced each year to satisfy these needs.

Maleic anhydride can be prepared commercially by the selective partial oxidation of suitable starting materials, such as benzene, butene or butane, with an oxygen-containing gas using an appropriate catalyst. Both fluidized bed reactors and fixed-tube heat-exchanger type reactors can be used for such partial conversions, and the details of the operation of such reactors are well known to those skilled in the art. Generally, the reaction to convert the hydrocarbons to maleic anhydride requires only passing the hydrocarbon admixed with a free-oxygen containing gas, such as air or oxygen-enriched air, through a vanadium-type catalyst at elevated temperature. The hydrocarbons are passed through the catalyst at a concentration of about 1.5 to about 10 volume percent hydrocarbon at a space velocity of about 100 to 4,000 cc/cc/hour at temperatures between about 350° C. and 600° C. In such processes, a gaseous reaction mixture is produced which contains from about 0.5 to about 2% by volume of the anhydride together with byproducts such as carbon monoxide, carbon dioxide, water vapor, inert gases, and the like.

The prior art also discloses a number of methods of recovering the maleic anhydride from the gaseous reaction mixture leaving the reactor. As an example, the maleic anhydride can be recovered by direct condensation and this method is widely used in commercial operations. On the other hand, the prior art also discloses that the maleic anhydride can be absorbed in a suitable solvent with subsequent separation and purification of the anhydride. As an example, British patent specification No. 763,339 discloses a process for scrubbing maleic anhydride from gaseous reaction mixtures using dibutyl phthalate as the solvent, and thereafter stripping the maleic anhydride from the solvent in two steps, each under critically controlled conditions, to recover the maleic anhydride. U.S. Pat. No. 2,574,644 describes a process for the recovery of both phthalic anhydride and maleic anhydride using dibutyl phthalate as the solvent, and thereafter separating each anhydride by modifying the operating conditions in the recovery steps. British patent specification No. 727,828 also describes a process for the recovery of phthalic anhydride and maleic anhydride in a gaseous reaction mixture wherein the reaction mixture is passed in contact with a dibutyl phthalate solvent for simultaneous absorption of both anhydrides, and stripping the absorbed anhydrides from the solvent. U.S. Pat. No. 3,891,680 discloses a process for the recovery of maleic anhydride from gaseous reaction mixtures by contacting the gaseous reaction mixture with a dialkyl phthalate ester having 4 to 8 carbon atoms in each alkyl group and a total of 10 to 14 carbon atoms in both alkyl groups.

Although maleic anhydride can be recovered from gaseous reaction mixtures using these and other processes in the prior art, all of these processes contain one or more disadvantages. As an example, in the conventional method of recovering maleic anhydride from gas mixtures by condensation, only about half of the maleic anhydride is recovered, and the gaseous reaction mixture must be processed further by other methods to recover the remainder of the maleic anhydride. In another method, the gaseous reaction mixture is scrubbed with water and the resulting aqueous mixture of maleic anhydride is dehydrated by azeotropic distillation with xylene. This recovery process has the drawback of converting a fair amount of maleic anhydride into fumaric acid, which in turn, causes yield losses and plugging problems in the maleic anhydride recovery sections of the plant.

The prior art processes using phthalate esters as the solvent teach that the maleic anhydride must be stripped from the solvent in two steps, each under critically controlled conditions, to separate the maleic anhydride from the solvent. Some processes relate to the recovery of a mixture of maleic anhydride and phthalic anhydride from gaseous reaction mixtures, but in today's commercial market these anhydrides are seldom produced as a mixture, but are generally produced in relatively high purity in plants designed to produce either maleic anhydride or phthalic anhydride. Other processes contemplate the use of solvents which are expensive or thermally unstable or unsuitable for other reasons for use in a commercial operation.

These and other disadvantages of the prior art are overcome by the process of the present invention. By the process of the present invention, greater than 98% of the maleic anhydride can be recovered from a gaseous reaction mixture using a solvent that is thermally stable, and which does not require multiple stripping steps under critically controlled conditions to separate the maleic anhydride from the solvent. Furthermore, although the process is suitable for the recovery of maleic anhydride obtained by the partial oxidation of benzene, it is particularly applicable to the recovery of maleic anhydride in a gaseous reaction mixture obtained by the partial oxidation of an olefin, such as butene, or of a saturated aliphatic hydrocarbon, such as butane, since it is known to those skilled in the art that the gaseous reaction mixture from the partial oxidation of an aliphatic hydrocarbon contains a greater amount of water vapor than does the gaseous reaction mixture from the partial oxidation of benzene. By the process of the present invention, the maleic anhydride is almost quantitatively removed from the gaseous reaction mixture using the solvent of the present invention, while at the same time maleic anhydride can be recovered from the solvent in a one-step stripping operation with an overall process efficiency of greater than 98 percent.

SUMMARY OF THE INVENTION

These and other advantages are achieved in a process for the recovery of maleic anhydride from a gaseous reaction mixture wherein the gaseous reaction mixture containing the maleic anhydride is contacted with a solvent to remove the maleic anhydride from the gaseous reaction mixture, and the solvent is stripped of the maleic anhydride at a temperature between about 200° C. and about 250° C., at a pressure less than about 760 torr, the temperature being below the thermal decomposition point of the solvent at the existing pressure, the improvement which comprises contacting the gaseous reaction mixture with a solvent comprising a dialkyl phthalate having 2 to 8 carbon atoms in each alkyl chain and from about 0.5 to about 10 weight percent phthalic anhydride.

Broadly described, maleic anhydride is produced by passing a hydrocarbon, such as benzene, butene or butane, admixed with air through a reactor containing an oxidation-type catalyst wherein the hydrocarbon is partially oxidized to maleic anhydride. The gaseous reaction mixture from the reaction containing from 0.5 to about 2 mole percent maleic anhydride and from about 4 to about 20 mole percent water vapor is cooled to a temperature above the dew point of the water in the gaseous reaction mixture. Then, the gaseous reaction mixture is contacted with a solvent which comprises a dialkyl phthalate having 2 to 8 carbon atoms in each alkyl chain and up to about 10 weight percent phthalic anhydride to absorb the maleic anhydride in the solvent. Small amounts of lower boiling components, i.e., hydrocarbon oxidation by-products, such as water, acetic acid, acrylic acid, and the like, are also absorbed in the solvent. The resulting solvent, which contains up to 25 weight percent maleic anhydride or more, is then continuously stripped of the maleic anhydride in a stripping-distillation column to remove the lower boiling by-products and to isolate the crude maleic anhydride. The solvent leaves the bottom of the column at a temperature between about 200° C. and 250° C., and then is cooled for recycling to the scrubbing step. The crude maleic anhydride isolated from the stripping step is accumulated and then distilled under vacuum to produce purified maleic anhydride. The regenerated solvent is cooled and filtered to remove small amounts of fumaric acid which otherwise would begin to accumulate and precipitate on heat transfer surfaces. A small side stream of the regenerated solvent is also periodically removed and purified by distillation to remove soluble tars. The distilled solvent is then recombined with the filtered solvent for recycle to the top of the absorber.

In one embodiment of this invention, a vapor stream of the lower boiling components and a small amount of maleic anhydride from the condenser of the stripping-distillation column in the stripping step, which comprises maleic anhydride, water and acrylic acid, is passed to a "sponge absorber" to recover the maleic anhydride from the vapor stream. In the sponge absorber, the vapor stream is contacted with solvent to remove maleic anhydride from the lower boiling components, which are discharged from the system. The solvent in the sponge absorber can be the same solvent as is used in the absorption step, and this is preferred. On the other hand, if a lower boiling solvent is used in the absorption step, a sponge absorber using a higher boiling solvent can be used to contact the vapor stream from the stripping-distillation column, or even the gaseous reaction mixture leaving the continuous countercurrent absorber, to recover maleic anhydride and lower boiling solvent in the stream or mixture. As will occur to those skilled in the art, the maleic anhydride, the lower boiling solvent and the higher boiling solvent must be separated from each other, and for simplicity, it is preferred to use the same solvent in the sponge absorber and in the absorber column. When the same solvent is used, the solvent containing the maleic anhydride can be stripped of the maleic anhydride simply by passing the solvent to the stripping-distillation column, or it can be returned to the absorber step to absorb more maleic anhydride from the gaseous reaction mixture, and this is preferred.

The process for the partial oxidation of various hydrocarbons to maleic anhydride is known to those skilled in the art. The reaction to convert hydrocarbons to maleic anhydride requires only passing the hydrocarbons admixed with a free-oxygen containing gas, such as air or oxygen-enriched air, through an oxidation catalyst at elevated temperatures. The hydrocarbons are passed through the catalyst at a concentration of about 1.5 to about 10 volume percent hydrocarbon, at a space velocity of about 100 to 4,000 cc/cc/hour to provide from about 0.5 to about 2.0% by volume maleic anhydride in the gaseous reaction mixture. It will be recognized by those skilled in the art that the type of maleic anhydride reactor, and the type and concentration of hydrocarbon in the feed gas will affect the mole percent maleic anhydride and the mole percent water vapor in the gaseous reaction mixture which leaves the reactor.

The gaseous reaction mixture containing the maleic anhydride is then cooled to a temperature, preferably below about 200° C., but above the dew point of the water in the gaseous reaction mixture. When the gaseous reaction mixture is cooled to a temperature below the dew point of water, maleic anhydride, or other components, these materials will accumulate on the walls of the equipment and block gas flow. Generally, for a gaseous reaction mixture containing about 1 volume percent maleic anhydride and about 10 volume percent water vapor, the gaseous reaction mixture should be cooled to a temperature between about 60° and about 200° C., preferably between about 100° and about 150° C.

The cooled gaseous reaction mixture is then scrubbed with a solvent to absorb the maleic anhydride from the gaseous reaction mixture while passing most of the water, acetic acid, acrylic acid, inert gases, carbon monoxide and carbon dioxide in the gaseous reaction mixture out of the scrubbing step. The temperature of the solvent that is introduced into the scrubbing step can vary within wide limits. Normally, the solvent is introduced into the scrubbing step at a temperature below about 75° C., both to enhance the absorption of the maleic anhydride in the cooler solvent and to reduce solvent losses. However, there does not seem to be an economic advantage to using solvent at temperatures much below about 20° C., and for a gaseous reaction mixture containing about 0.2 to about 1 mole percent maleic anhydride and up to about 10 mole percent water, the solvent introduced into the scrubbing step should be at a temperature between about 25° C. and 45° C., and more preferably, between 30° C. and 40° C.

The ratio of solvent to gaseous reaction mixture can also vary within wide limits, and it is preferred for reasons of economy that the solvent leaving the scrubbing step contain about 25 weight percent maleic anhydride. If the ratio of solvent to gaseous reaction mixture is too large, unnecessarily large quantities of solvent must be processed in subsequent steps. On the other hand, if the ratio of solvent to gaseous reaction mixture is low, excessive losses of maleic anhydride may occur. Thus, it can be seen that the ratio of solvent to gaseous reaction mixture also depends on the amount of maleic anhydride in the gaseous reaction mixture. For a gaseous reaction mixture containing about 0.7 mole percent maleic anhydride and about 7 mole percent water, the ratio of solvent to gaseous reaction mixture between about 0.07 and 0.3 kilograms per cubic meter is preferred, and it is even more preferred that the ratio of solvent to gaseous reaction mixture is between about 0.1 and 0.2 kilograms of solvent per cubic meter of gaseous reaction mixture.

The solvent, which is at a temperature between about 50° C. and about 150° C., containing the dissolved maleic anhydride is then stripped of the maleic anhydride by passing the rich solvent into a stripping-distillation column at a pressure between about 25 and 75 torr. The maleic anhydride is driven up the column and condensed at a temperature between about 60° C. and 75° C. It is preferred to condense the maleic anhydride at a temperature between about 65° C. and 75° C. while maintaining the stripping column at a pressure between about 40 torr and 60 torr, and even more preferably, the condense the maleic anhydride at a temperature between 66° C. and 70° C. while maintaining the stripping column at a pressure between about 48 and 52 torr.

The solvent from the stripping step exits the bottom of the stripping column at a temperature of at least 200° C. but below about 250° C., say 225° C. to 250° C., at reduced pressure to reduce the maleic anhydride concentration in the solvent to about 0.3 weight percent. Thereafter, the solvent is cooled, preferably filtered, and then recycled to the scrubbing step. The temperature and pressure at the bottom of the stripping column is important since its controls the maleic anhydride content in the solvent that is recycled from the stripping step to the scrubbing step. As will occur to those skilled in the art, the maleic anhydride content in the solvent that is introduced into the scrubber strongly influences the maleic anhydride recovery in the scrubbing step. Thus, when the solvent at the bottom of the stripping column is less than about 200° C., the amount of maleic anhydride in the solvent prevents the solvent from being as efficient in the scrubbing step; however, when the solvent is at too high of a temperature, excessive decomposition of the dialkyl phthalate occurs. It is preferred to maintain the solvent in the bottom of the stripping column at temperatures between about 240° C. and 250° C., say about 245° C.

Any number of dialkyl phthalate compounds having from two to eight carbon atoms in each alkyl chain known to those skilled in the art can be used as one component of the solvent. It is only necessary that the dialkyl phthalate has the desired solubility for maleic anhydride, has a relatively low vapor pressure at the temperatures used in the process of the present invention, and has sufficient thermal stability to avoid excessive decomposition. Suitable dialkyl phthalate compounds include diethyl phthalate, ethylbutyl phthalate, ethylpropyl phthalate, ethylisopropyl phthalate, propylbutyl phthalate, dibutyl phthalate, diisobutyl phthalate, butylamyl phthalate, diamyl phthalate, dihexyl phthalate, amylhexyl phthalate, diheptyl phthalate, butylheptyl phthalate, ethylheptyl phthalate, butylheptyl phthalate, dioctyl phthalate, ethyloctyl phthalate, propyloctyl phthalate, butyloctyl phthalate, and the like. Mixtures of two or more dialkyl phthalates are also satisfactory. Many of these compounds are commercially available, but all are readily obtainable, as will occur to those skilled in the art, by the diesterification of phthalic acid or phthalic anhydride with an alcohol containing 2 to 8 carbon atoms. Dibutyl phthalate is preferred.

The amount of phthalic anhydride in the dialkyl phthalate for use as the solvent in the process of the present invention is critical since it controls the temperature at which the solvent can be heated. The solvent comprises dialkyl phthalate and up to about 10 weight percent phthalic anhydride. If the dialkyl phthalate contains less than about 0.5 weight percent phthalic anhydride, the dialkyl phthalate may be over-heated in the bottom of the stripping-distillation column, causing excessive decomposition of the dialkyl phthalate. On the other hand, if the solvent comprises dialkyl phthalate and more than about 10 weight percent phthalic anhydride, the desired maleic anhydride may be contaminated with undesirable amounts of the phthalic anhydride from the solvent. It is preferred to use a solvent that contains from about 0.5 to about 5 weight percent phthalic anhydride in dialkyl phthalate, which will reduce the maleic anhydride concentration in the solvent to less than about 1 weight percent by heating to temperatures between about 240° C. and about 250° C. at less than atmospheric pressure. For example, if the solvent comprises dibutyl phthalate and about 1.25 percent phthalic anhydride by weight, the solvent will boil at a temperature of no more than about 246° C. at about 87 torr, when the maleic anhydride concentration in the solvent has been reduced to less than 0.5 weight percent.

The maleic anhydride from the stripping operation can be purified by any number of techniques known to those skilled in the art, as for example, by distillation at 140° C. at about 100 torr. Thereafter, the purified maleic anhydride can be treated with materials known to prevent the formation of color bodies in the maleic anhydride, such as small amounts of hydrochloric acid, metallic halides and the like. The product can then be used in commerce.

BRIEF DESCRIPTION OF THE DRAWING

The single drawing represents a flow diagram illustrating a preferred embodiment of the process of the present invention.

FURTHER DESCRIPTION OF THE DRAWING

Referring now to the drawing, a gaseous reaction mixture from the partial oxidation of a hydrocarbon is introduced through rich gas line 11 to the bottom of an absorber column 12. Solvent is then introduced into absorber column 12 near the top through lean solvent line 13. The gaseous reaction mixture is then contacted with the solvent in absorber column 12 to remove the maleic anhydride from the gaseous reaction mixture, which is discharged from the system through vent line 14. The solvent containing the maleic anhydride leaves absorber column 12 through rich solvent line 15 from a point near the bottom of absorber column 12 and introduces the solvent containing the maleic anhydride to a point near the middle of stripper (stripping-distillation) column 16. In stripper column 16, the solvent containing the maleic anhydride is heated at pressure below 760 torr, and the maleic anhydride from the solvent rises in stripper column 16 and is condensed near the top and removed as a liquid from stripper column 16 through crude MAN line 17, and passes to a maleic anhydride purification stage (not shown). The solvent, passes through stripper column 16 to a reboiler pot 18, containing a heater 19, which provides heat for the stripper-distillation and maintains the solvent at a temperature between about 200° C. and about 250° C. to reduce the maleic anhydride concentration in the solvent. The solvent is then removed from reboiler pot 18, preferably cooled and filtered in cooler-filter 41, and fed through recycle solvent line 20 to solvent storage tank 21 where make-up solvent is added through make-up solvent line 22. About 10 percent of the solvent is recycle solvent line 20 is removed and purified by distillation in solvent still 42 to remove soluble tars from the solvent.

The lower boiling components, mostly water and acrylic acid, which enter stripper column 16 with the solvent containing the maleic anhydride, are concentrated away from the point that crude maleic anhydride is isolated and withdrawn from stripping column 16 through crude MAN line 17. The condensation is conducted at conditions which will permit most of these lower boiling components to exit stripper column 16 through vent line 23 as vapor, but some of the maleic anhydride is also passed as a vapor through vent line 23. Thus, an absorption is carried out in the sponge absorber 30 to recover this maleic anhydride under substantially the same temperature and pressure parameters as used in the top of stripper column 16. The vapor stream from stripper column 16 passes to sponge absorber 30 through vent line 23, and is contacted in sponge absorber 30 with solvent entering sponge absorber 30 from lean sponge line 32. The solvent then removes the maleic anhydride from the lower boiling components, and this solvent containing the maleic anhydride is returned to absorber column 12 through sponge solvent line 33, and the lower boiling components stripped of the maleic anhydride in sponge absorber 30 are discharged from the system through jet line 34.

DESCRIPTION OF THE PREFERRED EMBODIMENTS

The invention will now be described in one embodiment of the process as disclosed in the drawing to recover about 454 kilograms of maleic anhydride.

Into absorber column 12 are simultaneously fed about 18,000 cubic meters of gaseous reaction mixture containing about 0.75 mole percent maleic anhydride at a pressure of about 915 torr, and at a temperature of about 145° C. to 155° C., and about 2,200 kilograms of solvent at a temperature between about 32° C. and 36° C. The solvent is a mixture of dibutyl phthalate containing 1.24 weight percent phthalic anhydride. The solvent enters twenty-tray absorber column 12 through lean solvent line 13, and contacts the gaseous reaction mixture in absorber column 12. The gaseous reaction mixture enters the bottom of absorber column 12 through rich gas line 11, and after being contacted with the solvent, exits the top of absorber column 12 through vent line 14, at a temperature between about 56° C. and 60° C., and a pressure between about 825 torr and 885 torr. The solvent, rich in maleic anhydride, leaves the 20-tray absorber column 12 through rich solvent line 15 at a temperature between about 101° C. and 105° C. In absorber column 12 the solvent absorbs about 99.4% of the maleic anhydride, about 0.6% of the water, 10% of the acetic acid and 53% of the acrylic acid, permitting the remaining gaseous reaction mixture to pass through vent line 14.

The solvent, rich in maleic anhydride, passing through rich solvent line 15, is introduced onto the fifth tray of the 12-tray stripper column 16. The maleic anhydride in the solvent will be driven up stripper column 16 and condensed at a temperature between about 66° C. and 70° C., at a pressure between about 48 torr and 52 torr, refluxed in the stripper column 16 and removed as liquid reflux from the 11th tray at an external reflux ratio of 2:1 through crude MAN line 17. The solvent passes through stripper column 16 to reboiler pot 18, where heat is provided to maintain the temperature between about 244° C. and 248° C., at a pressure between about 85 torr and 89 torr. Under these conditions, the maleic anhydride concentration in the solvent is reduced to about 0.3 weight percent. The solvent is then pumped from reboiler pot 18 through cooler-filter 41 and then to solvent storage tank 21 through solvent line 20 where about 10 percent of the solvent is purified by distillation in solvent still 42.

The lower boiling components, mostly water and acrylic acid which enter stripper column 16 with the solvent rich in maleic anhydride, are concentrated away from the crude maleic anhydride which is isolated and removed at the eleventh tray through crude MAN line 17 by the top two trays in stripper column 16, and these lower boiling components will exit stripper column 16 and go to sponge absorber 30, where an absorption is carried out to recover the maleic anhydride that is passed as vapor with the lower boiling components. In the sponge absorber 30, the vapor stream from stripper column 16 is contacted with solvent depleted in maleic anhydride, which enters sponge absorber 30 through lean sponge line 32, leading from solvent storage tank 21. The solvent contacts the vapor stream from stripper column 16 at a temperature of about 65° C. to recover about 77% of this maleic anhydride. The solvent, rich in maleic anhydride from sponge absorber 30, leaves sponge absorber 30 through sponge solvent line 33, which enters absorber column 12 at about the fifth tray. The unabsorbed portion of lower boiling components is passed from the sponge absorber 30 through jet line 34.

The crude maleic anhydride leaving stripper column 16 through crude MAN line 17 is cooled to a temperature between about 70° C. and 80° C., and is thereafter refined by distillation. From 98.5 to 99% of the maleic anhydride in the gaseous reaction mixture is recovered in the process.

Although the invention has been described in terms of specified embodiments which are set forth in considerable detail, it should be understood that this is by way of illustration only and that the invention is not necessarily limited thereto since alternative embodiments and operating techniques will become apparent to those skilled in the art view of the disclosure. Accordingly, modifications are contemplated which can be made without departing from the spirit of the described invention.

What is claimed is:

1. In a process for the recovery of maleic anhydride from a gaseous reaction mixture wherein the gaseous reaction mixture containing the maleic anhydride is contacted with a solvent to remove the maleic anhydride from the gaseous reaction mixture, and the solvent is stripped of the maleic anhydride at a temperature between about 200° C. and about 250° C. at a pressure less than 760 torr, the temperature being below the thermal decomposition point of the solvent at the existing pressure, the improvement which comprises contacting the gaseous reaction mixture with a solvent comprising a dialkyl phthalate having 2 to 8 carbon atoms in each alkyl chain and from about 0.5 to about 10 weight percent phthalic anhydride.

2. In a process of claim 1 wherein the solvent comprises from about 0.5 to about 5 weight percent phthalic anhydride.

3. In a process of claim 1 wherein the solvent comprises dibutyl phthalate.

4. In a process of claim 1 wherein the solvent comprises dibutyl phthalate and from about 0.5 to 5 weight percent phthalic anhydride.

5. In a process of claim 1 wherein the solvent is stripped of the maleic anhydride at a temperature between about 200° C. and 250° C. at a pressure between about 25 torr and about 100 torr.

6. In a process of claim 1 wherein the solvent is stripped of the maleic anhydride at a temperature between about 240° C. and about 250° C. at a pressure between about 75 torr and about 100 torr.

7. In a process of claim 1 wherein the solvent is stripped of maleic anhydride and lower boiling components, a portion of the maleic anhydride is isolated, and the lower boiling components containing maleic anhydride are contacted with solvent to recover maleic anhydride from lower boiling components.

8. A process for recovering maleic anhydride from a gaseous reaction mixture which comprises:

A. contacting in a scrubber the gaseous reaction mixture, which is at a temperature below about 200° C. but about the dew point of water in the gaseous reaction mixture, with a solvent at a temperature between about 20° C. and about 75° C., the solvent comprising dibutyl phthalate and from about 0.5 weight percent to about 5 weight percent phthalic anhydride, based on the weight of the dibutyl phthalate;

B. passing the solvent at a temperature between about 50° C. and about 150° C. into a stripping-distillation column maintained at a pressure between about 25 torr and about 100 torr;

C. maintaining the solvent in the bottom of the stripping-distillation column at a temperature between about 225° C. and 250° C. to remove lower boiling components and maleic anhydride from the solvent;

D. isolating crude maleic anhydride at a temperature between about 60° and 75° C.;

E. contacting the lower boiling components with solvent to remove maleic anhydride from the lower boiling components; and F. removing maleic anhydride from the solvent from Step E.

* * * * *

UNITED STATES PATENT OFFICE
CERTIFICATE OF CORRECTION

PATENT NO. : 4,118,403
DATED : October 3, 1978
INVENTOR(S) : James E. White

It is certified that error appears in the above–identified patent and that said Letters Patent are hereby corrected as shown below:

Column 9, line 24, "about" should be --above--.

Signed and Sealed this

Twenty-second Day of May 1979

[SEAL]

Attest:

RUTH C. MASON
Attesting Officer

DONALD W. BANNER
Commissioner of Patents and Trademarks